US010369071B2

(12) United States Patent
Klassen

(10) Patent No.: US 10,369,071 B2
(45) Date of Patent: Aug. 6, 2019

(54) EXOSKELETON SUIT WITH HAND CONTROL TO ENABLE WALKING

(71) Applicant: GENESIS ROBOTICS AND MOTION TECHNOLOGIES CANADA, ULC, Langely (CA)

(72) Inventor: James Brent Klassen, Langley (CA)

(73) Assignee: GENESIS ROBOTICS & MOTION TECHNOLOGIES CANADA, ULC, Langley (CA)

(*) Notice: Subject to any disclaimer, the term of this patent is extended or adjusted under 35 U.S.C. 154(b) by 412 days.

(21) Appl. No.: 15/309,422

(22) PCT Filed: May 5, 2015

(86) PCT No.: PCT/CA2015/050394
§ 371 (c)(1),
(2) Date: Nov. 7, 2016

(87) PCT Pub. No.: WO2015/168788
PCT Pub. Date: Nov. 12, 2015

(65) Prior Publication Data
US 2017/0181916 A1    Jun. 29, 2017

Related U.S. Application Data

(60) Provisional application No. 61/988,888, filed on May 5, 2014.

(51) Int. Cl.
*A61H 3/00* (2006.01)
*B25J 13/02* (2006.01)
(Continued)

(52) U.S. Cl.
CPC ............... *A61H 3/00* (2013.01); *A61F 2/72* (2013.01); *A61F 5/0102* (2013.01); *B25J 3/04* (2013.01);
(Continued)

(58) Field of Classification Search
CPC ............... A61F 2/70; A61F 2002/6827; A61F 2005/0155; A61H 2201/1207;
(Continued)

(56) References Cited

U.S. PATENT DOCUMENTS 3,358,678 A    12/1967  Kultsar
2008/0238352 A1  10/2008  Dattilo et al.

FOREIGN PATENT DOCUMENTS

GB    2 301 776 A    12/1996
JP    2013208342 A    10/2013
(Continued)

OTHER PUBLICATIONS

International Search Report for PCT/CA2015/050394, dated Aug. 25, 2015, 4 pages.
(Continued)

*Primary Examiner* — Brian A Dukert

(57) ABSTRACT

An exoskeleton suit allows a user to control the legs using the arms. Preferably, there is two-way feedback/control between the legs and arms causing movement of leg joints to be proportional to movement of arm joints. Haptic forces and control forces on the joints may also be proportional. The relative magnitudes of the movements and forces may be adjustable. Rotary or angular actuators may be used. A twisting actuator is also provided using a pair of bending actuators mounted side by side to provide torsional displacement of frame members. The ability to support a portion of the user's weight on the hand grips is possible while simultaneously controlling the lower body movement by applying pitch, roll and yaw movements to that hand grip.

12 Claims, 12 Drawing Sheets

(51) Int. Cl.
*A61F 2/70* (2006.01)
*A61F 5/01* (2006.01)
*B25J 3/04* (2006.01)
*B25J 9/00* (2006.01)
*A61F 2/72* (2006.01)
*A61F 2/50* (2006.01)
*A61F 2/68* (2006.01)

(52) U.S. Cl.
CPC ........... *B25J 9/0006* (2013.01); *B25J 13/025* (2013.01); *A61F 2002/5038* (2013.01); *A61F 2002/6827* (2013.01); *A61F 2002/701* (2013.01); *A61F 2005/0155* (2013.01); *A61H 2201/1207* (2013.01); *A61H 2201/164* (2013.01); *A61H 2201/1635* (2013.01); *A61H 2201/5058* (2013.01)

(58) Field of Classification Search
CPC .... A61H 2201/1635; A61H 2201/5061; A61H 2201/164; A61H 2201/5058; A61H 2003/005; A61H 2003/007; A61H 3/00; B25J 13/025; B25J 13/02; B25J 9/0006
See application file for complete search history.

(56) References Cited

FOREIGN PATENT DOCUMENTS

| | | |
|---|---|---|
| WO | 2008/094191 A2 | 8/2008 |
| WO | 2011/002306 A1 | 1/2011 |

OTHER PUBLICATIONS

Office Action received for corresponding Japanese Application No. 2016-566938, dated Apr. 9, 2019, 12 pages—including translation.

EXOSKELETON SUIT WITH HAND CONTROL TO ENABLE WALKING

CROSS-REFERENCE TO RELATED APPLICATIONS

This application claims the benefit under 35 U.S.C. § 119(e) of U.S. provisional application Ser. No. 61/988,888, filed May 5, 2014.

BACKGROUND

Technical Field

Exoskeleton suits.

Description of the Related Art

The human brain is highly adaptive. It will reprogram and even rewire itself to make use of new and different sensory information if the original information is no longer available. This process of rewiring is referred to as brain plasticity.

In brain plasticity experiments, it has been shown that with haptic (touch sense) feedback to an alternate skin patch, an amputee's brain well decode that feeling as coming from the prosthetic finger tips. In another example, if a person has lost the balance function of their inner ear, an electronic transducer generating impulses on the user's tongue will be decoded by their brain as coming from the inner ear so the person can resume walking or even riding a bike.

Paraplegic people will benefit from being confined to a wheelchair. Exoskeleton suits offer the potential for this freedom. Existing exoskeleton suits that predict their intent with a computer algorithm provide increased mobility, but the person's movements are still determined by a computer program that will never be able to predict their every intent.

BRIEF SUMMARY

The present exoskeleton suit design harnesses the computing power and adaptive motion control capability of the human brain. It provides the user with a level of haptic feedback and control that will give an amputee or paraplegic a true sense of freedom and mobility. Able-bodied users will also benefit from the principles of operation of this device in certain applications.

Learning to use the present device may take longer than a conventional system because creating neural connections can take three weeks or more to become "hardwired" into the human brain. This is not a downside of the system performance. It is a potential benefit. The inventor of the present application has observed that the process of discovery, breakthrough, and improvement, consistently result in a sense of accomplishment, satisfaction and happiness.

An embodiment of the present device exoskeleton suit will provide the potential for high mobility and a high level of user control. Undulations of the ground will be felt in the user's hands through the haptic feedback handles. At the same time, movement of the hands (while a button is pressed on that handle—similar to a mouse button) will control the position, lateral angle, and rotation of the feet.

Within a few weeks or months of practice, for some users, the brain may begin to decode the haptic feedback to the hands and the user may begin to regain what the brain will perceive this feeling in their hands as feeling in their feet. At the same time, the brain may begin to perceive the haptic input movement which they can feel in their hands and arms as signals as if they are being relayed directly from the legs and feet.

Instead of crutches, as are common to other exoskeleton suits, the actuator technology used for the suit can be of the rotary type which include, but are not limited to strain wave rotary actuators, and will preferably be responsive enough to allow the hand grips to support the user's weight through the structure without the need for crutches.

Accordingly, there is provided an exoskeleton suit having hand grip members configured to receive a user's hands. The hand grip members are configured to be moved by the user when the user's hands are received by the hand grip members. Sensors in the frame and/or actuators are configured to detect the movement of the hand grip members as input to the system by the user moving his or her hands. Foot receiving or foot emulating members are provided, and actuators are configured to move the foot receiving or foot emulating members according to the movement detected by the sensors configured to detect the movement of the hand grip members.

In various embodiments, there may be included any one or more of the following features: there may be control elements on the hand grip members; the exoskeleton suit being configured to select which foot receiving or foot emulating member is moved according to the movement of which hand grip member according to signals from the control elements; the control elements may also have a neutral setting, the exoskeleton suit being configured in the event of a control element being set to a neutral setting to allow a hand grip member to move freely without a corresponding foot movement; there may be ground contact sensors on the foot receiving or foot emulating members, and feedback actuators on the hand grip members connected to receive information from the ground contact sensors to give the user feedback as to which part of the foot receiving or foot emulating members is contacting the ground and with what level of contact pressure; the feedback given to the user by each feedback actuator may have a signal strength depending on a respective ground contact pressure detected by one or more respective ground contact sensors; the actuators configured to move the foot receiving or foot emulating members may be configured to move according to the movement detected by the sensors configured to detect the movement of the hand grip members with a relative magnitude of motion which is adjustable by the user; the control elements may, for example, be pressure sensitive and the relative magnitude may be adjustable based on the pressure sensed by the control elements; there may be sensors configured to detect movement of the foot receiving or foot emulating members, and actuators configured to move the hand grip members according to the movement detected by the sensors configured to detect movement of the foot receiving or foot emulating members; the actuators configured to move the hand grip members may be configured to move according to the movement detected by the sensors configured to detect movement of the foot receiving or foot emulating members with the inverse of the relative magnitude of motion adjustable by the user; the actuators configured to move the hand grip members may be connected in pairs with the actuators configured to move the foot receiving or foot emulating members; each actuator being associated with a force sensor detecting a force applied or received by the respective actuator; the actuators of each pair being configured to apply a force depending on the force detected by the force sensor of the other actuator of the pair to maintain a predetermined relative magnitude of forces for the pair; the predetermined relative magnitude of forces for each pair may be adjustable by the user; the actuators configured to move the hand grip members include actuator assemblies as defined the following paragraphs; and the actuators configured to move the foot receiving or foot emulating members include actuator assemblies as defined in the following paragraphs.

There is also provided an actuator assembly having a first end portion, a second end portion, a first longitudinal element extending between and connecting the first end portion and the second end portion, a second longitudinal element extending between and connecting the first end portion and the second end portion, the first longitudinal element separated from the second longitudinal element in a first lateral direction, the first longitudinal element being activatable to bend in a second lateral direction substantially perpendicular to the first lateral direction and the second longitudinal element being activatable to bend in an opposite direction to the second lateral direction, the bending of the first longitudinal element in the second lateral direction and the bending of the second longitudinal element in the direction opposite to the second lateral direction causing twisting of the actuator assembly to cause relative rotation of the first end portion and the second end portion.

In various embodiments, there may be included any one or more of the following features: the first longitudinal element and second longitudinal element may be activatable to bend in directions opposite to the directions of the bending causing the twisting of the actuator assembly to cause an opposite twisting of the actuator assembly; the actuator assembly may be configured to be capable of causing a rotation of 45 degrees or more of the second end portion relative to the first end portion with each of the twisting and the opposite twisting; the actuator assembly may be configured to be capable of causing a rotation of 90 degrees or more of the second end portion relative to the first end portion with each of the twisting and the opposite twisting; the first longitudinal element may comprise a first piezoelectric, or other active material, actuator and may be activatable to bend by activation of the first piezoelectric actuator and the second longitudinal element may comprise a second piezoelectric actuator and may be activatable to bend by activation of the second piezoelectric actuator; the actuator assembly may also be configured to detect twisting of the actuator assembly by detecting voltage generated by the twisting in at least one of the first piezoelectric actuator and the second piezoelectric actuator; the actuator assembly may be used in an upper arm, lower arm, lower leg, or upper leg portion of an exoskeleton for a human; the actuator assembly may be used in an upper arm, lower arm, lower leg, or upper leg portion of an anthropomorphic robot; and the actuator assembly may be used in an arm of an industrial or other type of robot or motion control member.

These and other aspects of the device and method are set out in the claims, which are incorporated here by reference.

BRIEF DESCRIPTION OF THE SEVERAL VIEWS OF THE DRAWINGS

Embodiments will now be described with reference to the figures, in which like reference characters denote like elements, by way of example, and in which.

DETAILED DESCRIPTION

Figure 1:
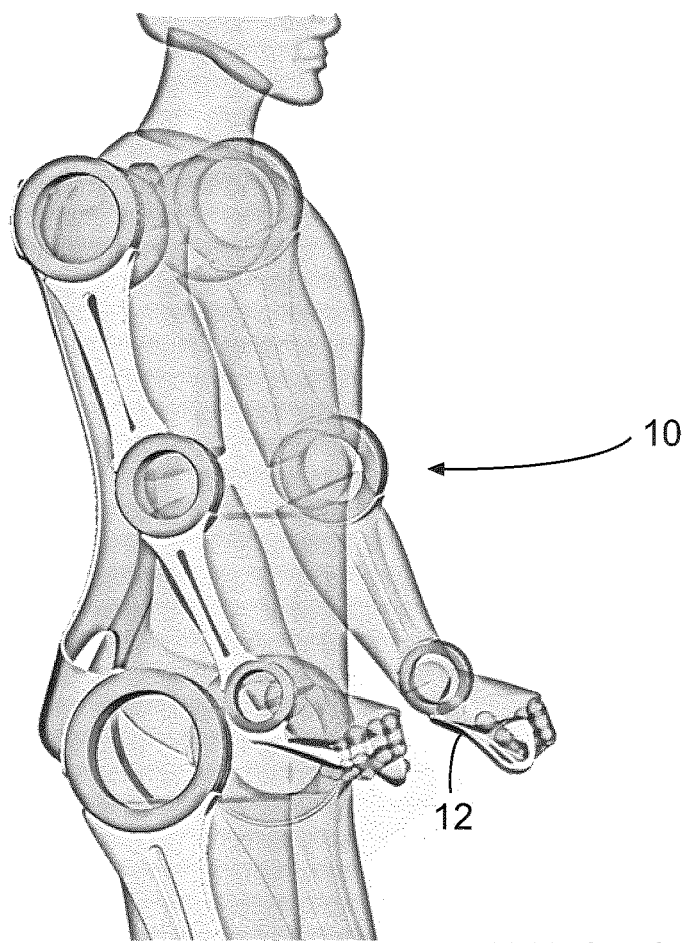
FIG. 1 is a side view of an upper body of a person wearing an exoskeleton suit.
Figure 2:
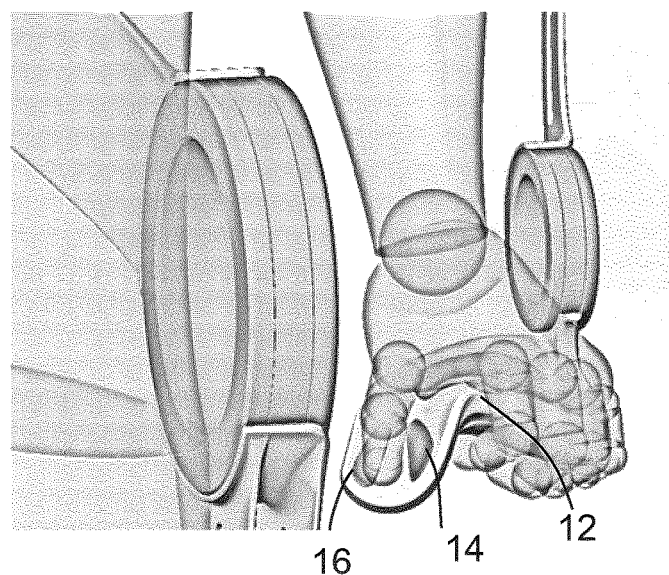
FIG. 2 is a close-up front view of a handgrip of the exoskeleton suit of FIG. 1.
Figure 4:
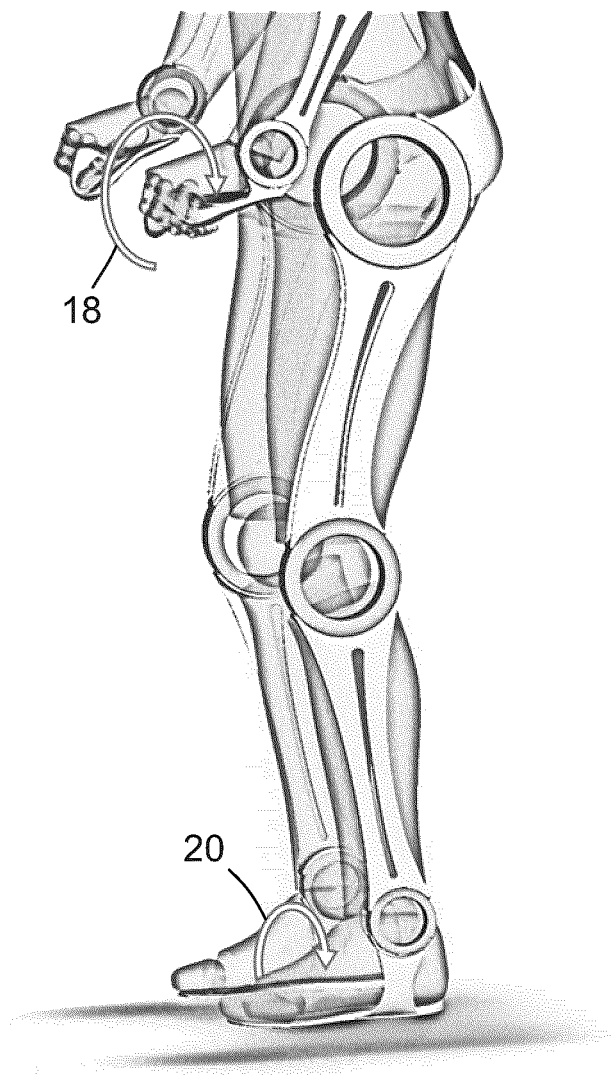
FIG. 4 is a side perspective view of a lower body portion of the exoskeleton suit of FIG. 3.

An exemplary embodiment of an exoskeleton suit 10 comprises one or more hand grip members or hand grips 12 as shown in FIG. 1 and FIG. 2. The hand grips are multifunctional. They provide control as well as haptic feedback from the lower body. Tilting a hand grip to the right (clockwise) will tilt one of the feet to the right. Which foot a grip controls is determined by which button on that grip is activated. In a preferred embodiment, both hand grips have a button to activate each of the left and right feet/legs. When the left button 14 on one of the grips is activated by the user on either of the grips (in this exemplary embodiment, the left thumb button on each grip), any movement of that grip and/or arm will result in movement of the left leg as follows:

Left clockwise rotation of grip as indicated by arc 18 in FIG. 4=left clockwise rotation of foot as indicated by arc 20 in FIG. 4.

Forward rotation of grip=forward rotation of foot.

Flexion of elbow=flexion of knee.

Outward rotation of shoulder=outward rotation of hip.

Forward rotation of shoulder=forward rotation of hip actuator.

Figure 3:
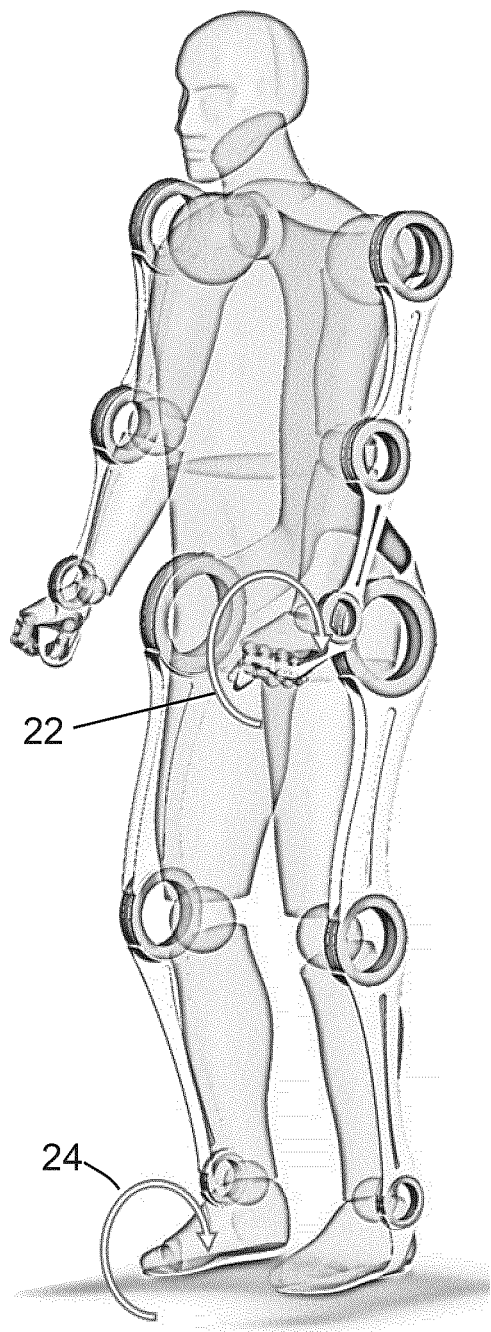
FIG. 3 is a full-body perspective view of a person wearing an exoskeleton suit.

Likewise, when right button 16 is activated, movement of the grip as indicated for example by arc 22 in FIG. 3 will result in movement of the right foot as indicated by arc 24 in FIG. 3.

In a preferred embodiment, the buttons are pressure sensitive so greater pressure on the button 14 or 16 will result in more movement of the corresponding leg and foot.

Personal settings for the amplification or attenuation of various types of movements will be helpful for user, for example, if they have limited movement in their upper body as part of their disability.

It is important to note that with a preferred embodiment of this system, the movement of the grips and arms only results in movement of the feet/legs if one of the buttons/pads 14 or 16 is pressed. If the buttons are not activated, the arms can move freely (for other tasks) without moving the legs.

The movement of the hand grip members is detected by sensors in the arm members and/or actuators. In a preferred embodiment, sensors associated with all the arm joints listed above detect the motion of each individual joint. Collectively, the detection of the movement of each joint detects the movement of the hand grip members. Actuators are configured to move lower body members according to the movement of upper body members detected by upper body sensors. This configuring may include, but is not limited to, control by a CPU. This movement of the foot receiving or foot emulating members may, in a preferred embodiment, be implemented by movement of each leg joint listed above according to the movement of the corresponding arm joint as input by the user and detected by the sensors. It is also possible, where the limbs have sufficient degrees of freedom, to move the foot receiving or foot emulating members according to the motion of the hand grip members without the movement of individual joints corresponding.

Haptic Feedback

Feedback from the lower body to the upper body is preferably as follows:

Any angulation of a foot resulting from contact with the ground or other object will result in an angular movement of a proportional magnitude and/or proportional force transmitted back to the hand grips and other joints in the reverse as stated above. For example, if the left foot steps on uneven ground such that it rotates counter clockwise (when viewed from behind), the hand grip with the left button pressed, will angulate the counterclockwise direction well. This movement can be a force that can resisted by the user (force feedback), or it can be a proportional movement (movement feedback) or a combination of both. The amount of force feedback vs movement feedback is preferably selected/or adjusted by user preference. Force feedback and movement feedback do not contradict one another. Even with the motions being fully constrained to match using movement feedback, this constraint can be met by the user to a greater degree through applying forces to the legs (as a result of input by the user to the upper body members) to make them match the motion of the arms with the intended relative magnitude. In other words, the user can apply a small force and/or movement to the arms to obtain a large force and/or movement in the legs. At the same time, the user can set the exoskeleton control to transmit a weak haptic feedback force to the upper body as a result of larger forces and/or movements which are experienced by the lower body members). Thus a relative magnitude of motion and legs and a relative magnitude of forces between associated joints of the arms and legs can be independently controlled. The relative magnitudes may be linear proportionalities or non-linear relationships.

As another example of the haptic feedback effect, the inertia of the lower limb being moved will preferably be sensed in the arm and hand grip of the arm and grip that is moving that foot/leg, and felt as greater resistance to movement the arm/grip.

Figure 5:
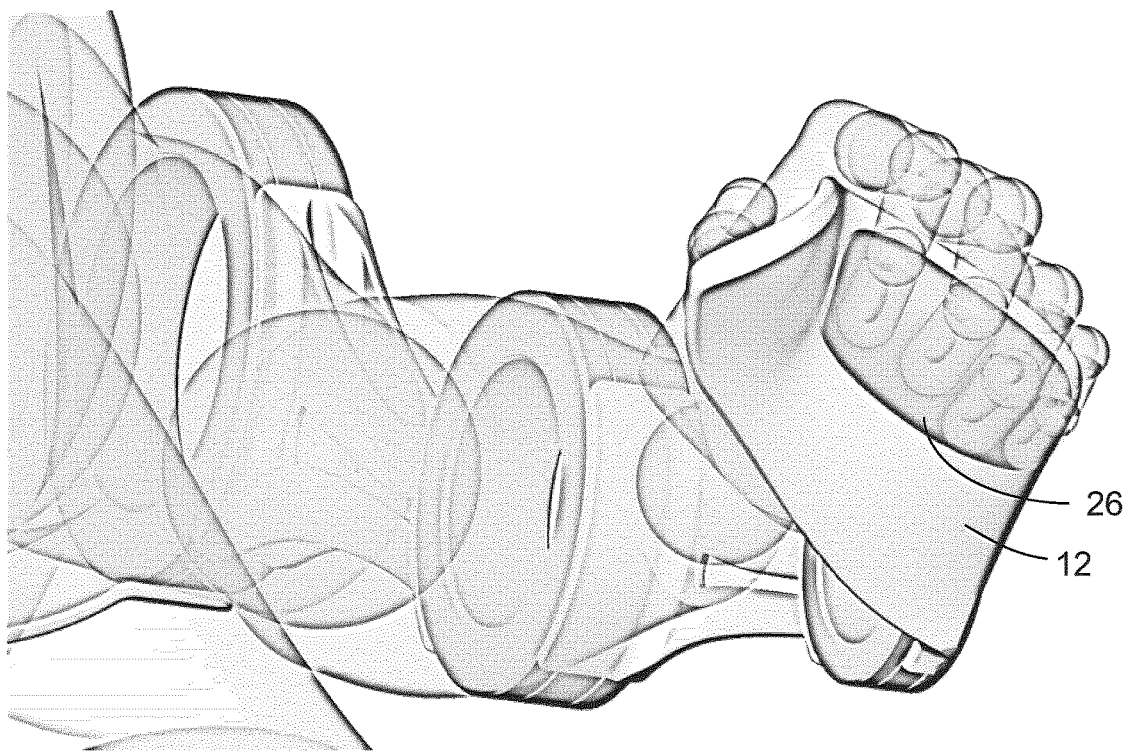
FIG. 5 is a perspective view of an arm portion of an exoskeleton suit showing a control pad on the underside of an arm grip.

The amount of haptic feedback is preferably controlled by the user with an input such as the button or pad 26 shown on the underside of the grip 12 in FIG. 5. To increase haptic feedback, in this exemplary embodiment of one of many ways for the user to input to the system to change the feedback amount, the user will apply more pressure with their fingertips. This will amplify the amount of force and/or movement that feeds back to that hand (or both hands, depending on user preference).

Figure 6:
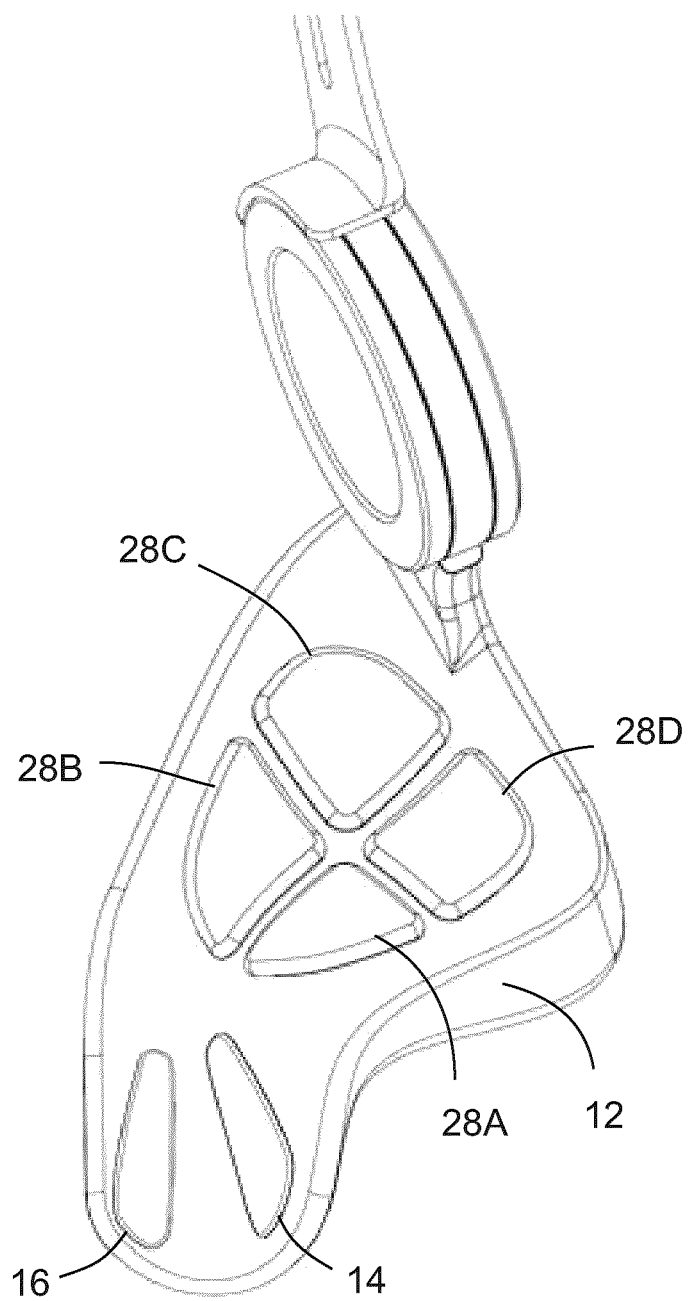
FIG. 6 is a close-up view of an hand grip of an exoskeleton suit showing control and feedback components normally covered by a user's hand during use of the exoskeleton.
Figure 7:
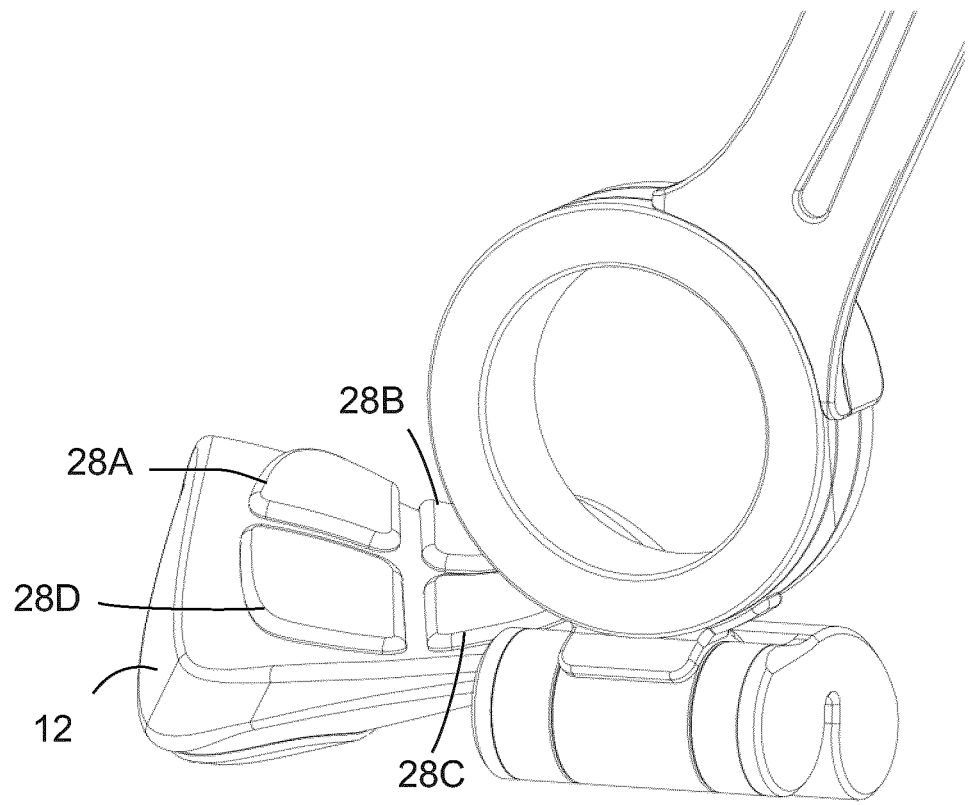
FIG. 7 and FIG. 8 are close-up views of another embodiment of a hand grip of an exoskeleton from different perspectives.
Figure 8:
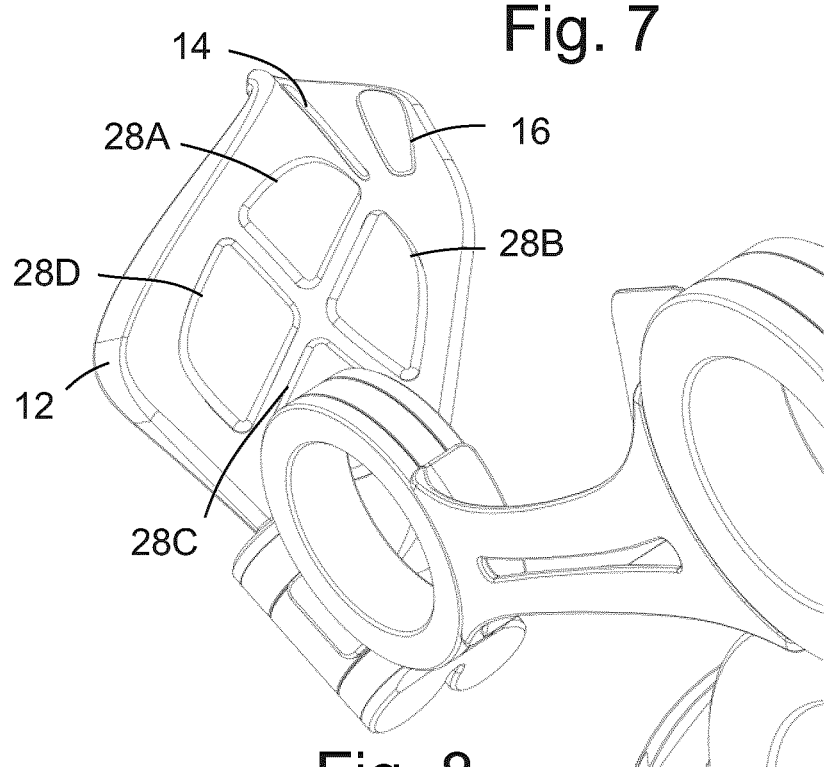

Another force feedback that is believed to be useful input to the user is a type of contact detection between the feet and the ground which is relayed via movement and/or electrical stimulation and/or vibration on a surface that is contacting the user's skin in an area that is sensitive to this input. A non-limiting example is shown in FIG. 6 where a pad under the user's palm is energized with a vibrating movement in one or more areas. In this example, the pad is split in 4 sections 28A, 28B, 28C and 28D which vibrate (or give indication by some user detectable means) more or less intensely depending on the pressure detected in the corresponding quadrant of the foot/shoe sole that is contacting the ground. This feedback will allow the user to sense the ground contact through their hands (and/or other skin area and/or visual and/or audio feedback but the palm contact area is believed to be a preferred feedback area for ground contact force haptic feedback). This ground contact feedback level can also be adjusted in real time or with a setting, by and/or for the individual user. With this feedback, it is believed possible for some users to stand on one foot, for example, and to make adjustments with a hand grip which cause precise angular corrections of the ground-contacting foot/ankle/leg. The importance of this additional feedback is due to the fact that the small angular movements that would be fed back to the user from the imbalance of standing on one foot (within the small range of angle that is necessary to maintain balance) would not necessarily be adequate to inform the user of when they are off balance. Standing on one foot is a more challenging example of what it is believed this suit will allow a user to do, but walking is a series of one foot movements that will all provide this feedback to the user in real time. So walking or even standing on two feet will provide the user with a constant awareness of pressure distribution on the foot contacting surface with the ground so a safe and effective ambulatory motion can be achieved. FIGS. 7 and 8 show another embodiment of a hand grip with similar vibrating pads 28A-28D for feedback from two perspectives.

Figure 9:
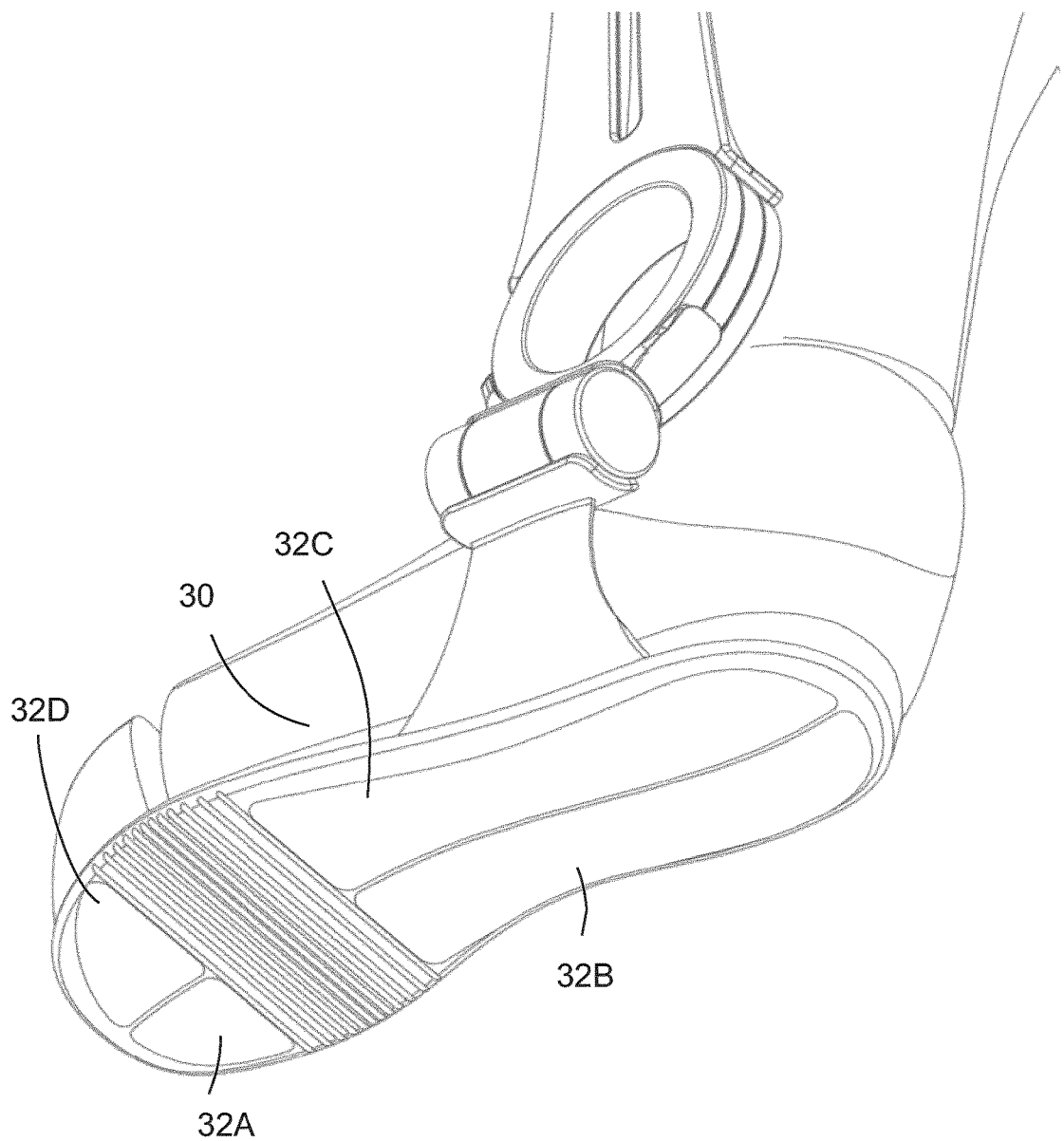
FIG. 9 is a perspective view of an underside of a foot portion of an exoskeleton suit showing pressure sensors.

The sensors located on the sole of the foot can be but are not limited to, piezoelectric, piezoresistive, or electromagnetic strain sensors. Ideally, each sensor will be able to detect ground contact pressures and/or forces within the range of what is typically experienced during standing, walking, and running, and will allow the user, through haptic feedback to the upper body members, to differentiate between small differences in pressure such that the user can make corrections before becoming off balance. FIG. 9 shows a foot portion 30 of an exoskeleton having pads 32A, 32B, 32C and 32D each having an associated pressure sensor (not shown) detecting pressure on the pad.

Many different control inputs are conceivable and have been anticipated by the inventor including but not limited to mechanical buttons, or non-moving pressure sensitive pads or buttons, or verbal commands or activation by other parts of the body other than the hands, such as head movement etc.

Operating the Suit

With the above input methods (or variations of methods consistent with the principles of the upper body movement, as input by the user, controlling the lower body movements), it is believed possible for the user to walk in this device (even if they have no ability to move all or part of their lower extremities on their own) by moving their hands and/or arms to affect input forces and/or movements to the upper body members of the suit, and in this way cause and control ambulatory movement of the lower body members of the suit.

Figure 10:
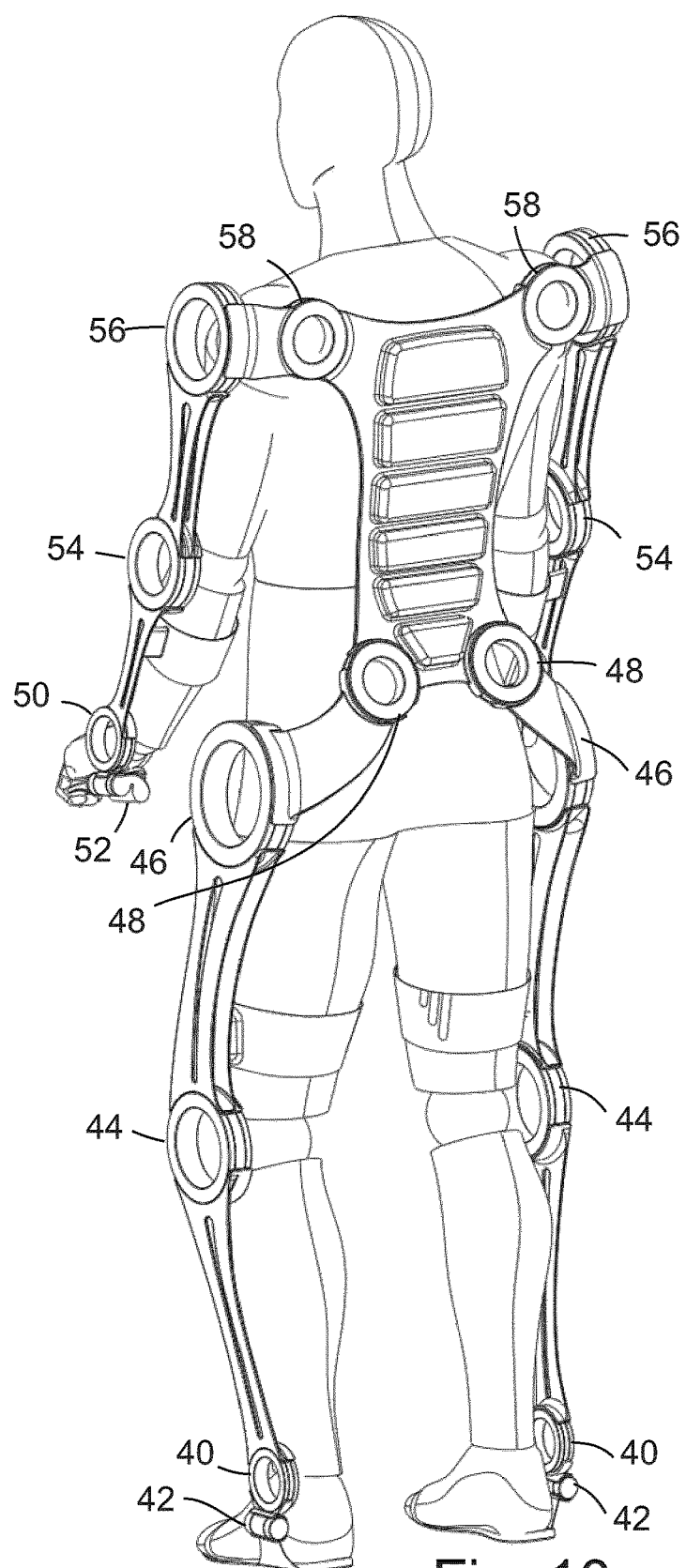
FIG. 10 is a perspective view of an exoskeleton suit showing various rotary or angular joints.

Each of the hollow cylindrical or long cylindrical members in the Figures represents a rotary or other actuation method of achieving angular torque and movement. Any rotary actuator may be used, however strain wave rotary actuators are preferred due to their high torque and low profile, allowing the exoskeleton to be less bulky than other actuation systems. This actuator can be magnetically-controlled, and can, for example, convert an input current into an output torque. Each actuator can, for example, allow rotation about a single axis, and by combining several actuators the hands and feet of the suit can move with up to six (6) degrees of freedom. The ideal number of actuators will vary with suit design and user needs. The suit shown in FIG. 10 is an example of the minimum number of actuators needed to provide full mobility. They consist of the following:

Rotary and/or Angular Actuators
  Ankle rotation joint 40—linked to wrist rotation joint 50.
  Ankle rolling joint 42—linked to wrist rolling joint 52.
  Knee joint 44—linked to elbow joint 54.
  Hip joint (forward/backward rotation) 46—linked to shoulder joint (forward/backward rotation) 56.
  Hip lateral rotation extension joint 48—linked to shoulder lateral rotation joint 58.

An embodiment of the present device exoskeleton contains two of each joint for the left and right sides of the body. One embodiment illustrating the preferred placement of each of these actuators is shown in FIG. 10.

In the preferred embodiment where the lower body joints are controlled by the upper body joints, each of these actuators will be linked in pairs. The link with each of the joints on one arm will be established to the joints of a leg corresponding to the thumb button that is pressed. The pairs of linked joints are, in one example, as follows:
  Clockwise (CW) Ankle rotation joint results from CW rotation of wrist joint (viewed from side).
  CW rolling of Ankle joint results lateral from CW lateral rolling of wrist joint (viewed from front).
  CW rotation of Knee joint results from Counterclockwise (CCW) rotation of elbow joint (viewed from side).
  CW Hip joint rotation results from CCW shoulder joint rotation (viewed from side).
  CW lateral Hip joint rotation results from CW lateral rotation of shoulder joint (viewed from front).
  Note that the haptic feedback will preferably have the same relationship (e.g., CW=CW or CW=CCW as listed above).

The exoskeleton suit could be designed so that all the limbs respond the same form upper to lower body (i.e., CW of upper actuator=CW of lower). But it will be much more intuitive for the user if that is true of all associations except the shoulder-hip association and the elbow-knee association. In these two cases, the rotation direction that is most natural (if you imagine moving your feet with your hand motion) is actually reversed.

Additional actuation means are necessary to achieve rotation of the foot and wrist in the yaw directions. This can be done in many different ways, but because these movements are lower torque than the pitch axis movement of the ankles and wrist, and because a movement like ankle roll is typically lower angular displacement than ankle or knee pitch, for example, there are more simple ways these movements can be accomplished.

Figure 11:
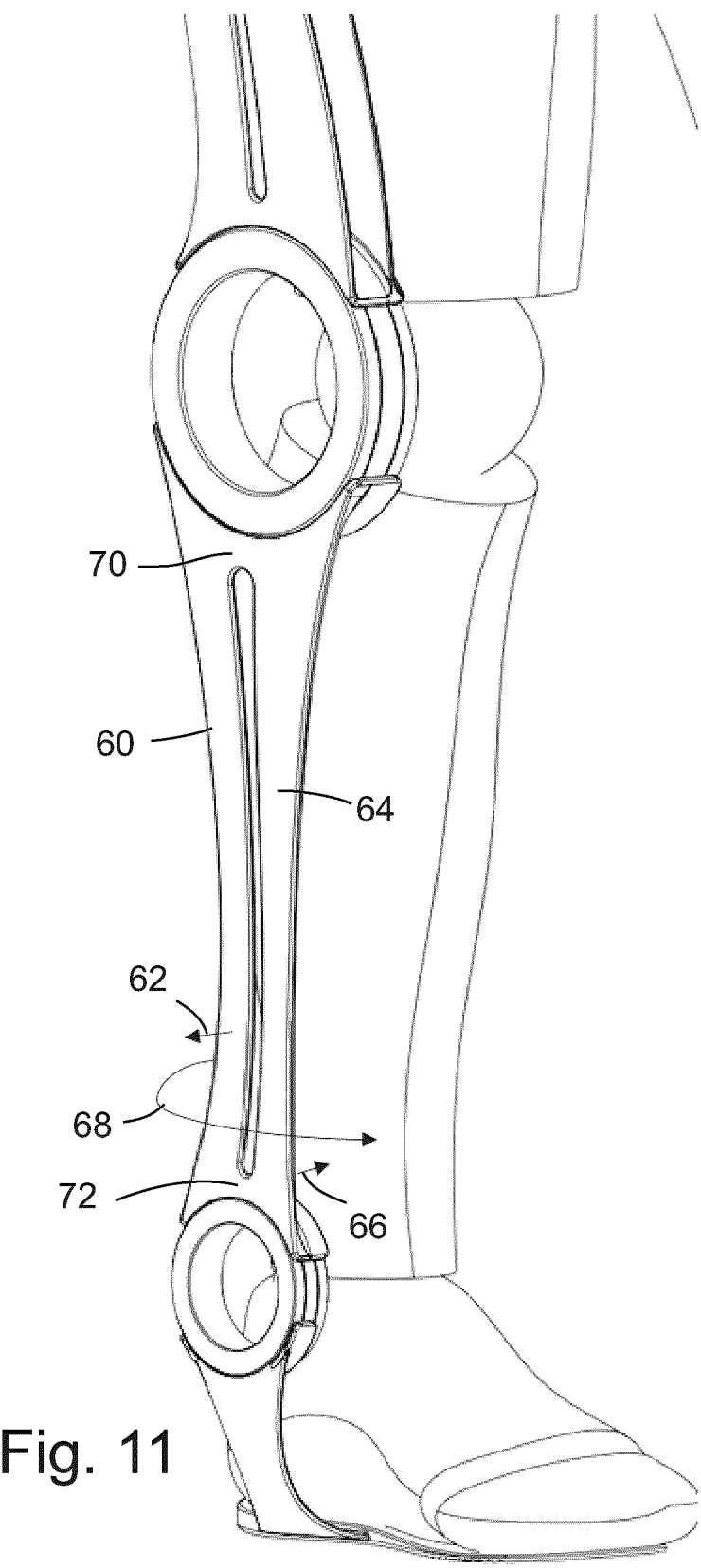
FIG. 11 is a close-up perspective view of a lower leg portion of an exoskeleton suit having a twisting capability.

One of many examples is shown in the Figures, with details in FIG. 11, with a "tib-fib" arrangement on all "limbs" of the present device exoskeleton.

By coating or laminating to the surface of the structural members analogous to the tibia and fibula of a human lower leg, a yaw movement can be created by shortening one side of one of the tib or fib members and shortening the opposite side of the other tib or fib member.

The structural members in this exemplary embodiment can be made of many different type of rigid material such as steel or plastic or composite material such as, but not limited to carbon fiber. The shortening of the surface (and or lengthening of the opposite side of each structural member) needs to be done by a material of mechanism that is capable of exerting enough force to create the requisite yaw deformation as a result of the opposing forces. Other types of movement can be accomplished with this strategy as well, such as roll angulation of the ankle structure by activating shortening and/or lengthening materials to one or both sides of the ankle support structure.

Suitable materials to achieve these movements include, but are not limited to piezo ceramics or electro-active materials. Heat activated materials such as nitinol, or mechanical or electromechanical or electromagnetic means of changing the shape and/or relative length of one or both sides of one or more of the tibia and fibula members in one or more of the exoskeleton suit limbs or other members may be used.

FIG. 11 illustrates an actuator assembly implementing yaw motion using a tib-fib structure with exemplary piezo material coating on the outer and inward surfaces. An applied voltage supplied by the CPU causes the piezo ceramic coating on longitudinal elements (tibia and fibula members) to contract. Activating the posterior outer surface to cause it to contract will cause the posterior member 60 to bend as indicated by arrow 62 and activating the anterior inward surface, causing it to contract, will cause the anterior member 64 to bend as indicated by arrow 66. The combined effect of these opposed bends will cause a twisting of the lower leg member as indicated by arrow 68 to cause a yaw rotation of the foot. End portions 70 and 72 connect the anterior and posterior members so that the bending effects cause rotation of the end portions with respect to one another. The magnitude of the bending effect can be controlled by the magnitude of the voltage supplied. The CPU regulates this voltage based on input from sensors in the arm members. If a similar arrangement is used in the arm members, the applied voltage generated in the piezo ceramic coating from the user's wrist movement is read by the CPU and used to calculate the voltage that is supplied to correspondingly contract the tibia and fibula members. In this way, a yaw movement in the hand can produce a corresponding yaw movement in the foot. Twisting the wrist or upper arm preferably results in a twist of the foot or upper leg members in the same direction. The use of the terms "anterior", "posterior", "inner" and "outer" are with respect to this particular example and should not be considered to limit the claims to a particular orientation. The actuator assembly as described can also be used in other limb portions of the exoskeleton and also in other applications such as anthropomorphic robots, where it can be used for example in upper or lower arm and leg portions as in the exoskeleton, and industrial or other types of robots or motion control mechanisms.

Weight Support
  With the device described here, and using rotary and other actuators with a fast and consistent motion, it is believed possible to allow the user to support a portion of their weight on the hand grips of the device without the use of an additional ground contacting member such as a crutch. This weight support through the exoskeleton frame is similar to the function of crutches, but the weight transfer from the hands to the ground is through the exoskeleton suit to the feet. With precise and responsive input control and motion feedback as described in this disclosure, it is believed possible for the user to support a portion of their weight on the hand grips while affecting movement of the feet and legs with hand/arm movement. For example, when the weight bearing foot is on the ground, the only movement of the corresponding grip that is necessary to create ambulatory movement, in one exemplary condition, is a rotation of the ankle and a small angular pitch and yaw rotation of the ankle for balance. The pitch and yaw rotation of the ankle can both be activated by user input control via associated hand grip pitch and yaw force and/or movement while they have part or all of their weight on this hand grip. Movement control of the pitch and yaw can be accomplished simultaneously to the same hand grip supporting the user's weight because the CPU and haptic feedback control algorithms will not allow the hand grip to move vertically downward unless the foot does. The foot is prevented from moving vertically by the ground, and the grip is prevented from moving vertically downward by the motion feedback control system, so the user can tilt the hand grip in any direction to achieve a corresponding tilting of the corresponding foot. At the same time, the user can apply a downward force on the hand grip that will not result in a downward movement of the foot (because the foot is contacting the ground) and so the user is able to support a portion of his or her weight on the vertically downward immovable hand grip.

By allowing the grips to move vertically only when the foot is free to move vertically and preventing the movement of the grips vertically when the foot is contacting the ground (this happens as a result of the motion feedback in the description above), the hand grip will not move down when weight is applied to it when the corresponding foot is on the ground. This will allow the user to support a portion of their weight on the hand grip, similar, the load carrying capacity ability, to how the force transfer through a common exoskeleton frame can be used to help people carry weight on their backs).

Figure 12:
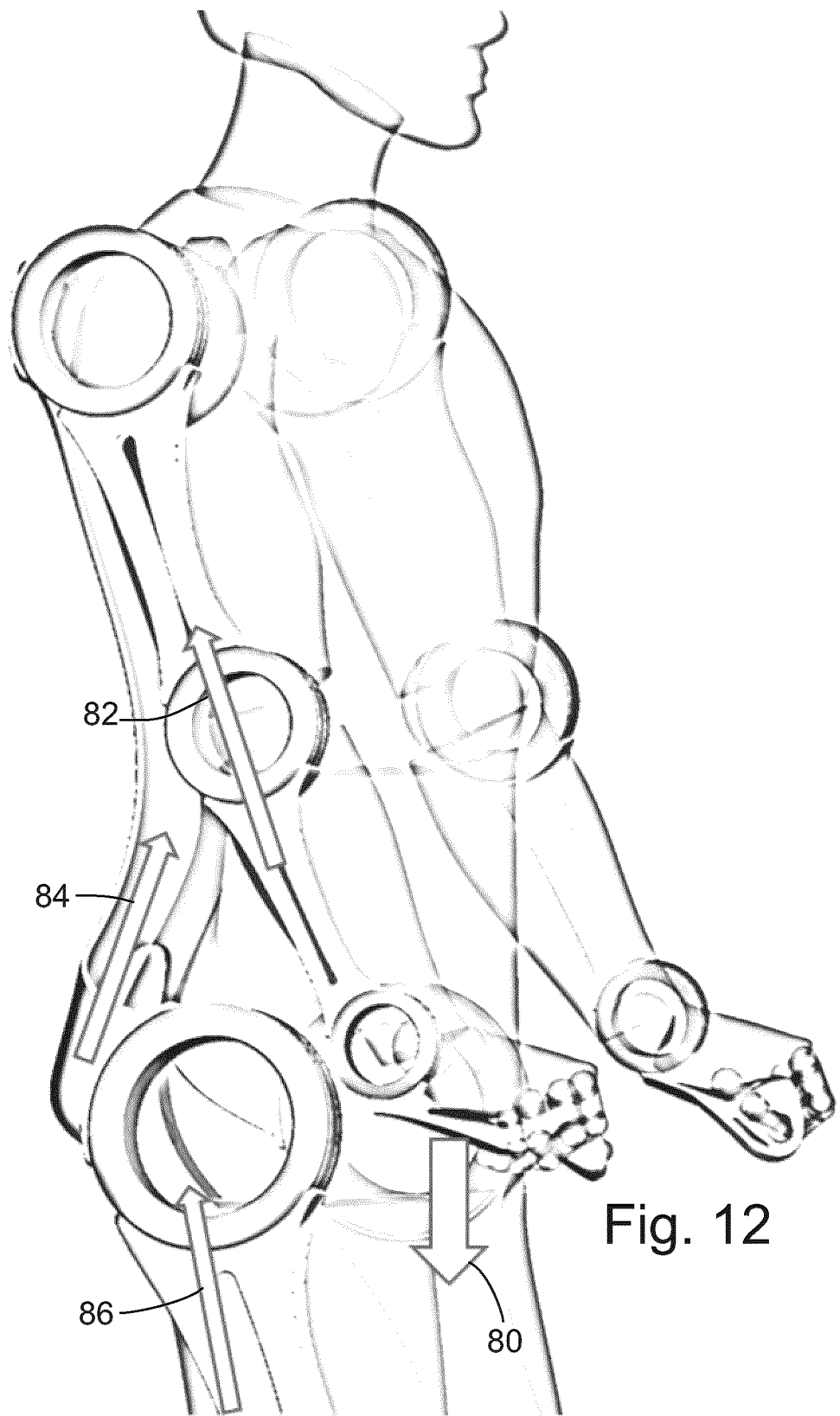
FIG. 12 is a side view of an upper body portion of an exoskeleton suit showing how force can be transmitted through the exoskeleton to allow the user to at least partially support their weight through their arms.

Thus principle is illustrated in FIG. 12. Arrow 80 indicates the downward force exerted by the user on hand grips 12. Arrows 82, 84 and 86 illustrate the transmission of forces through the exoskeleton via the feedback principles disclosed above which allows the hand grips to be supported by the exoskeleton against the force applied by the user to allow the user to support at least a portion of their weight through the hand grips while simultaneously controlling the movement of the feet with input of roll and yaw to said hand grip.

Control System

The control of the lower extremities by the movement of the upper extremities will preferably be though a CPU that is programmed according to the operating system and the user's preferences.

Figure 13:
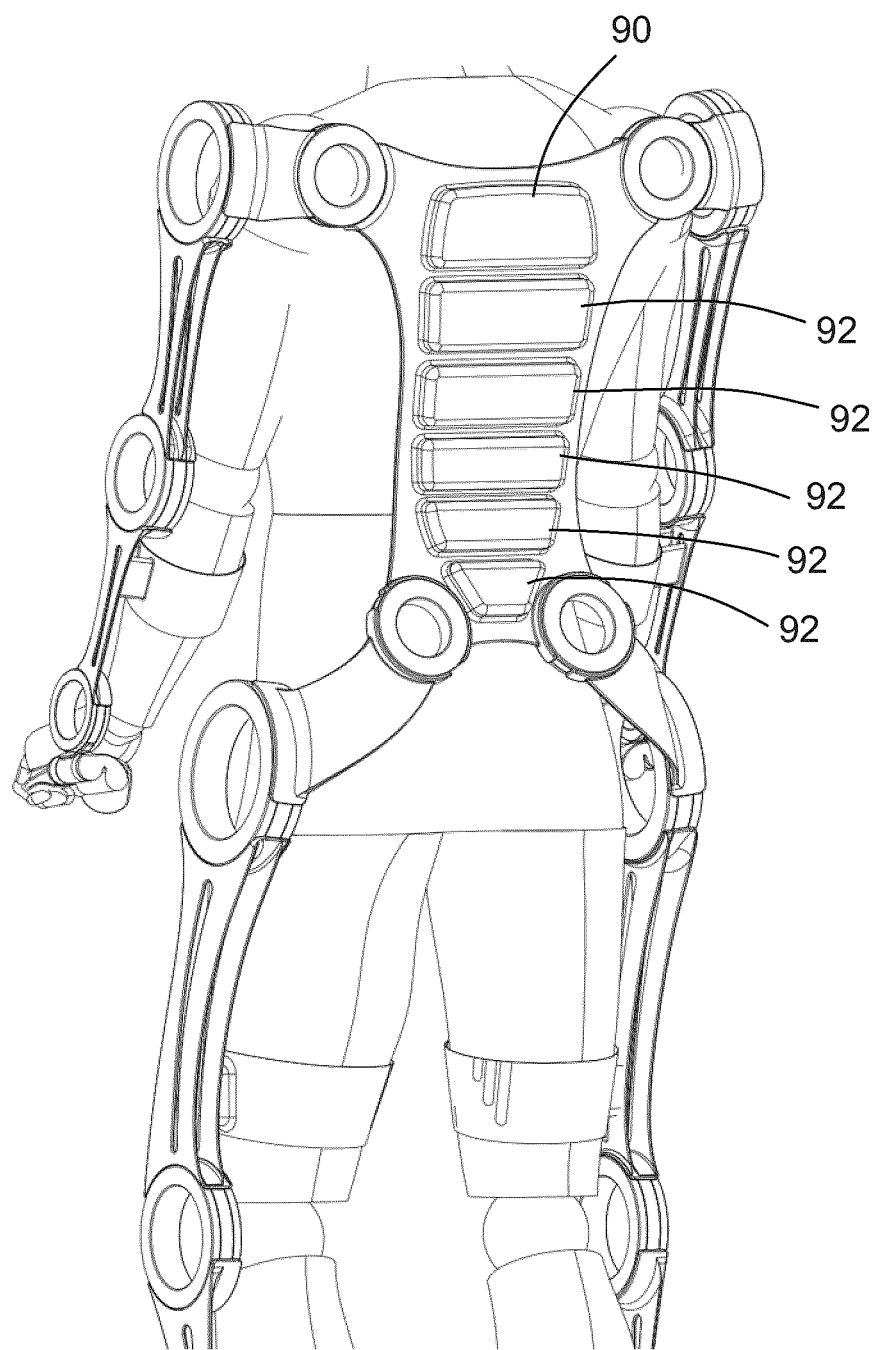
FIG. 13 is a rear perspective view of the exoskeleton suit showing a controlling CPU and battery packs.

In one embodiment shown in FIG. 13, a CPU 90 and one or more battery packs 92 will be attached to the back of the suit. Each of the 4 pads 32A-32D on the bottom of the foot (not shown in FIG. 13, but shown in FIG. 9) will contain a pressure sensor which will be connected to the CPU through wires (not shown) that run up the sides of the suit. The CPU will then send signals through a series of wires out to the hand grips to activate the pads below the palms of the user's hands with a signal corresponding to that measured by the pressure sensors.

Figure 14:
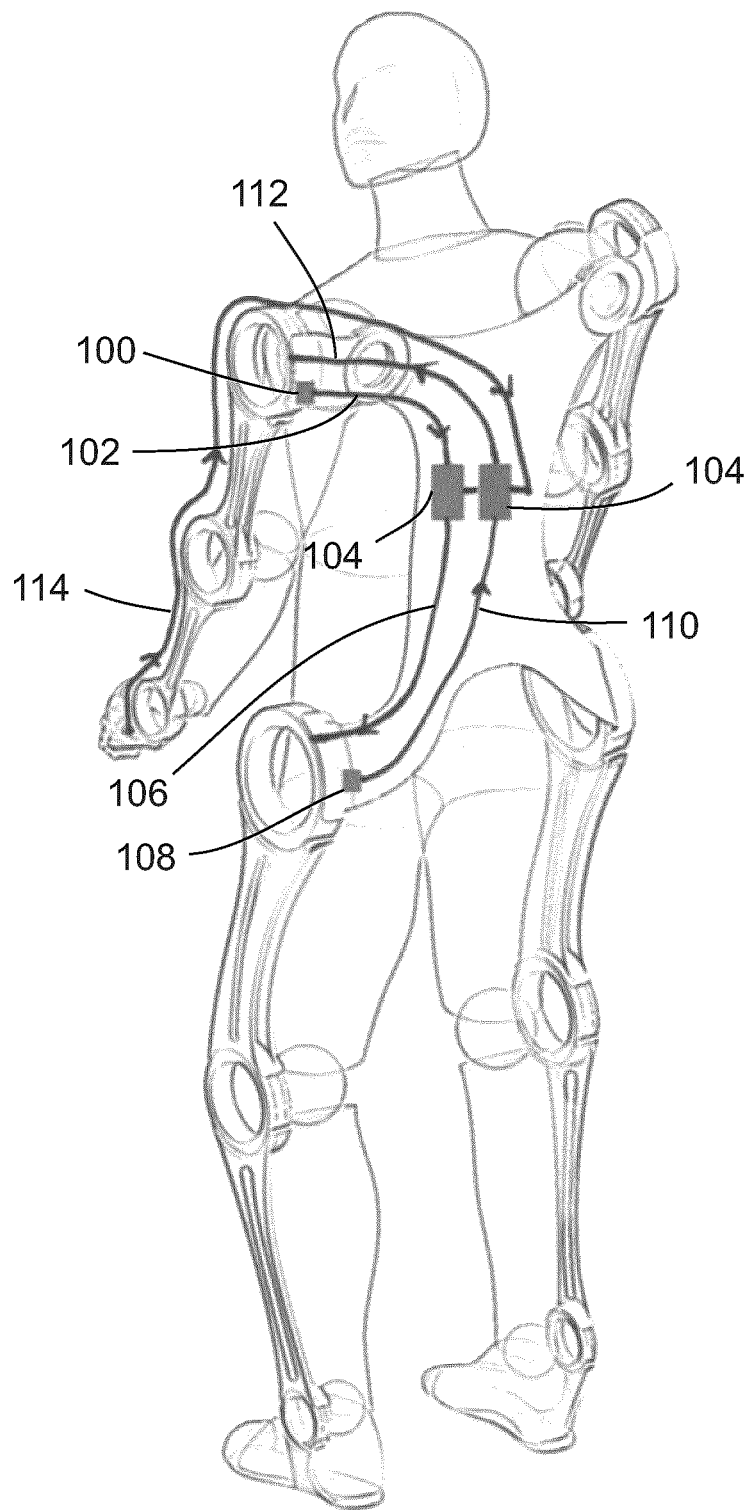
FIG. 14 is a rear perspective view of an exoskeleton suit showing exemplary signal paths.

In an embodiment where the actuators are magnetically actuated strain wave rotary actuators, control can be achieved in a simple way with minimal use of complex algorithms in the CPU to read and power each of the actuators individually. Rather, each connected joint will have a sensor which outputs a current that goes through either attenuation or amplification and directly powers the actuator of its corresponding joint in the opposite half of the body. Preferably, this connection will only be active when the user depresses the thumb button which establishes this connection between the joints of one arm and the joints in a corresponding leg. The amount of output current from each upper body sensor will be directly proportional to the external torque on the upper body actuators and/or upper body frame as input by the user, and as sensed by sensors. Each movement of an upper body actuator will result in a proportional movement of a corresponding lower body actuator as described above. The amount of attenuation/amplification of this movement and/or force from input actuator to output is preferably controllable by the user. This user control is preferably in real time with the button pressure applied (and/or in a user settings preference). In one embodiment, the sensor signal from the upper body going to the lower body can be amplified by the user increasing pressure on the thumb button, whereas the haptic feedback signal strength from the lower body to the upper body can be amplified by the user increasing pressure on a feedback button on the underside of the hand grip. In this way, each set of actuators will affect each other directly and will function using a motion and/or force scaling "tug-of-war" principle. When an outside force is applied to one, such as when a foot steps on an uneven surface, it causes a corresponding movement in the hand grip. The user can overcome this movement with an opposing force and/or movement, however they will experience resistance proportional to the force on the foot. The two joints will always be moving in proportional unison (when the movement button linking those two upper and lower body sections is pressed), however whichever force is greater in proportion to a ratio of force feedback between the upper and lower body joints (as described above), be it the upper or lower body force, will succeed in controlling the motion of the other. The user can preferably amplify or attenuate the effect of either signal through the use of the proportional hand buttons as described above. Even though the user may be providing a haptic feedback force from a foot to the corresponding hand that is larger, when modified by a feedback proportion level, than an opposite force on the foot (in other words, if the haptic feedback from the foot to the hand member is stronger than the user is able to overpower), the force at the hand rest member will still be felt by the user as resistance to their hand motion and any resistance by the user to the haptic feedback motion of the hand will translate into a counter-force signal to the foot member. In this way the user can allow the foot member to move with a controlled level of freedom which is dependent on the motion/force proportion level setting and the user strength or effort. A schematic of this feedback system between a hip and shoulder joint is shown in FIG. 14. Shoulder sensor 100 sends signal 102 to controller elements 104 which may include amplification/attenuation modules. Controller elements 104 accordingly send signal 106 to a hip actuator element. Hip sensor 108 sends signal 110 to controller elements 104 which accordingly send signal 112 to a shoulder actuator. Controller elements 104 modify signals 106 and 112 according to control signals 114 from hand buttons. Each pair of joints can be linked in this fashion through the sensors attached to the actuators.

The location of each sensor will depend on the type of sensor used. Possible sensors include torque sensors and angular position sensors. Each joint will have a sensor located on or nearby the actuator.

Both the control and the feedback system are preferably very fast acting so the motion and feedback happen in real time with no perceptible delay experienced by the user.

In an embodiment of the present device, the wrists actuators and sensors are coupled to the ankle actuators and sensors as described above, the elbows actuators and sensors are coupled to the knee actuators and sensors, and the shoulder actuators and sensors are coupled to the hip actuators and sensors.

Attachment

Figure 15:
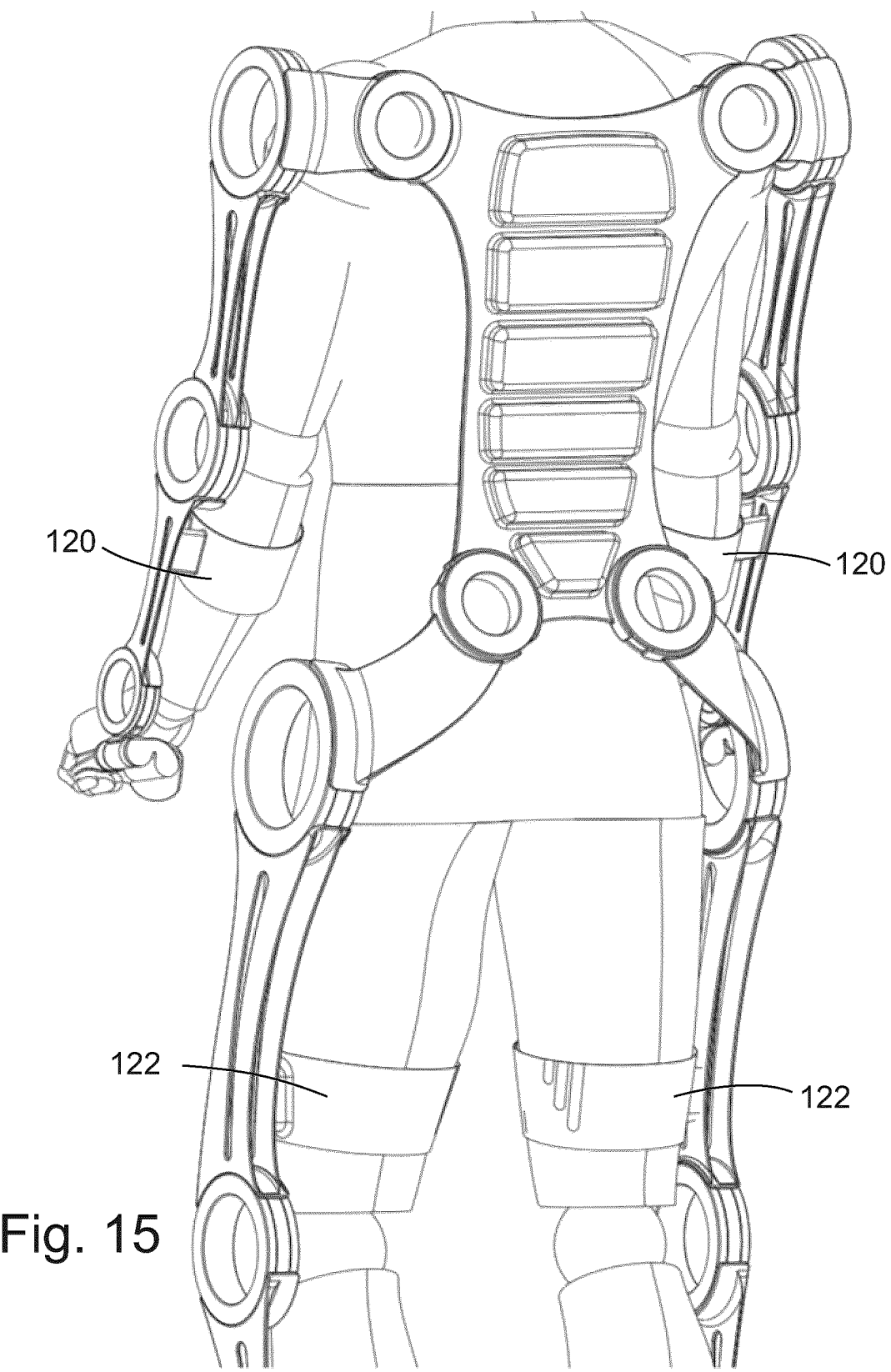
FIG. 15 is a rear perspective view of an exoskeleton suit attached to a human body using rigid clasps as an exemplary attachment mechanism.

The exoskeleton can attach to the body using many methods including but not limited to straps or clasps made from fabric, leather, plastic, or metal among other materials. The places of attachment can be anywhere along the limbs or the torso of the body. FIG. 15 illustrates an embodiment of an attachment system similar to that used in braces where the limb fits inside a rigid clasp that encircles the limb. Four attachments are shown: two clasps 120 on the lower arms and two clasps 122 on the upper legs. In some cases, surgical attachment may be preferable.

In another exemplary control strategy, the CCW rotation of the right shoulder actuator (rotation of shoulder actuator in this example is relative to the torso and viewed from the right side) results (by user selection of the right lower limb) in the CCW rotation of a knee actuator (rotation of knee actuator in this example is relative to the upper leg member and viewed from the right side). CCW rotation of the elbow actuator (relative to the upper arm and viewed from the right side) in this example, results in the CCW rotation of the slave hip actuator (relative to the torso and viewed from the right side). This control configuration allows the user to intuitively move a foot in any direction without consciously thinking about the shoulder or elbow movements. Haptic feedback in this exemplary control strategy variation is preferably in reverse of the control association (from the knee actuator back to the master shoulder actuator, and from a hip actuator back to the master elbow actuator.)

Another description of the above using different terminology is as follows: When the user chooses to move the right lower limb with the right upper limb, the anterior rotation of the right shoulder actuator results in the extension of the right knee actuator (the posterior rotation of the right shoulder actuator results in the flexion of the right knee actuator). Flexion of the right elbow actuator results in the anterior rotation/flexion rotation of the right slave hip actuator (and extension of the right elbow actuator, results in the posterior rotation/extension of the slave hip actuator).

Haptic feedback in this exemplary control strategy variation is preferably in reverse of the control association (from the slave knee as chosen by the user back to the master shoulder actuator, and from the slave hip actuator, as chosen by the user, back to the master elbow actuator).

As described above, in an embodiment of the present device, the user can choose to control the left or right lower limbs with the left or right upper limbs.

Many other control strategies are possible and conceived by the inventor. They include specific master actuators controlling specific slave actuators in different directions and to different proportions and in different combinations with various effects. The examples given here are intended as examples but are in no way intended as limits to how the suit can be configured or controlled.

Immaterial modifications may be made to the embodiments described here without departing from what is covered by the claims.

In the claims, the word "comprising" is used in its inclusive sense and does not exclude other elements being present. The indefinite articles "a" and "an" before a claim feature do not exclude more than one of the feature being present. Each one of the individual features described here may be used in one or more embodiments and is not, by virtue only of being described here, to be construed as essential to all embodiments as defined by the claims.

The embodiments of the invention in which an exclusive property or privilege is claimed are defined as follow:

1. An exoskeleton suit comprising:
    hand grip members configured to receive a user's hands, the hand grip members configured to be moved by the user when the user's hands are received by the hand grip members;
    sensors configured to detect the movement of the hand grip members;
    foot receiving or foot emulating members; and
    actuators configured to move the foot receiving or foot emulating members according to the movement detected by the sensors configured to detect the movement of the hand grip members, further comprising control elements on the hand grip members; the exoskeleton suit configured to select which foot receiving or foot emulating member is moved according to the movement of which hand grip member according to signals from the control elements.

2. The exoskeleton suit of claim 1 in which the control elements also have a neutral setting, the exoskeleton suit being configured in the event of a control element being set to a neutral setting to allow a hand grip member to move freely.

3. The exoskeleton suit of claim 1 further comprising ground contact sensors on the foot receiving or foot emulating members, and feedback actuators on the hand grips connected to receive information from the ground contact sensors to give the user feedback as to which part of the foot receiving or foot emulating members is contacting the ground.

4. The exoskeleton suit of claim 3 in which the feedback given to the user by each feedback actuator has a signal strength depending on a respective ground contact pressure detected by one or more respective ground contact sensors.

5. The exoskeleton suit of claim 1 in which the actuators configured to move the foot receiving or foot emulating members are configured to move according to the movement detected by the sensors configured to detect the movement of the hand grip members with a relative magnitude of motion which is adjustable by the user.

6. The exoskeleton suit of claim 1 in which
    the actuators configured to move the foot receiving or foot emulating members are configured to move according to the movement detected by the sensors configured to detect the movement of the hand grip members with a relative magnitude of motion which is adjustable by the user; and
    the control elements are pressure sensitive and the relative magnitude is adjustable based on the pressure sensed by the control elements.

7. The exoskeleton suit of claim 1 further comprising sensors configured to detect movement of the foot receiving or foot emulating members, and actuators configured to move the hand grip members according to the movement detected by the sensors configured to detect movement of the foot receiving or foot emulating members.

8. The exoskeleton suit of claim 5 further comprising sensors configured to detect movement of the foot receiving or foot emulating members, and actuators configured to move the hand grip members according to the movement detected by the sensors configured to detect movement of the foot receiving or foot emulating members in which the actuators configured to move the hand grip members are configured to move according to the movement detected by the sensors configured to detect movement of the foot receiving or foot emulating members with the inverse of the relative magnitude of motion adjustable by the user.

9. The exoskeleton suit of claim 7 in which the actuators configured to move the hand grip members are connected in pairs with the actuators configured to move the foot receiving or foot emulating members; each actuator being associated with a force sensor detecting a force applied or received by the respective actuator; the actuators of each pair being configured to apply a force depending on the force detected by the force sensor of the other actuator of the pair to maintain a predetermined relative magnitude of forces for the pair.

10. The exoskeleton suit of claim 9 in which the predetermined relative magnitude of forces for each pair is adjustable by the user.

11. The exoskeleton suit of claim 1 further comprising feedback actuators to provide feedback to upper body members and in which feedback from the feedback actuators is lower than or equal to the amount of force the user must input to the upper body members to overcome the haptic feedback force in the upper body members to generate opposing movement of lower body members.

12. The exoskeleton suit of claim 1 in which rotation of a shoulder joint controls the rotation of a knee joint.

* * * * *